US009353145B2

(12) United States Patent
Derrien et al.

(10) Patent No.: US 9,353,145 B2
(45) Date of Patent: May 31, 2016

(54) PROCESS FOR PREPARING 17-SUBSTITUTED STEROIDS

(71) Applicant: ZACH SYSTEM, Avrille (FR)

(72) Inventors: Yvon Derrien, La Meignanne (FR); Patricia Poirier, Saint Clement de la Place (FR); Massimiliano Forcato, Rovolon (IT); Tony Pintus, Saint Jean de Linieres (FR); Livius Cotarca, Cervignano Del Friuli (IT); Sebastien Meunier, Feneu (FR); Laurence Graindorge, Angers (FR)

(73) Assignee: ZACH SYSTEM, Avrille (FR)

(*) Notice: Subject to any disclaimer, the term of this patent is extended or adjusted under 35 U.S.C. 154(b) by 117 days.

(21) Appl. No.: 14/350,456

(22) PCT Filed: Oct. 9, 2012

(86) PCT No.: PCT/EP2012/069937
§ 371 (c)(1),
(2) Date: Apr. 8, 2014

(87) PCT Pub. No.: WO2013/053691
PCT Pub. Date: Apr. 18, 2013

(65) Prior Publication Data
US 2014/0256932 A1 Sep. 11, 2014

(30) Foreign Application Priority Data
Oct. 10, 2011 (EP) .................................. 11306310

(51) Int. Cl.
C07J 1/00 (2006.01)
C07J 43/00 (2006.01)
C07J 31/00 (2006.01)

(52) U.S. Cl.
CPC .............. *C07J 43/003* (2013.01); *C07J 1/0059* (2013.01); *C07J 31/003* (2013.01); *C07J 31/006* (2013.01)

(58) Field of Classification Search
CPC ........... C07J 1/00; C07J 31/006; C07J 43/003
USPC ............................................. 540/95; 552/636
See application file for complete search history.

(56) References Cited

U.S. PATENT DOCUMENTS

2007/0282109 A1 12/2007 Bury
2011/0288288 A1 11/2011 Bury

FOREIGN PATENT DOCUMENTS

| CN | 101768199 A | 7/2010 |
| EP | 0 633 893 | 1/1995 |
| EP | 0 721 461 | 7/1996 |
| EP | 1 789 432 | 5/2007 |
| WO | WO 93/20097 A1 | 10/1993 |
| WO | WO 95/09178 A1 | 4/1995 |
| WO | WO 2006/021776 A1 | 3/2006 |
| WO | WO 2006/021777 A1 | 3/2006 |

OTHER PUBLICATIONS

International Search Report issued Nov. 29, 2012, in PCT/EP12/069937 filed Oct. 9, 2012.
Written Opinion of the International Searching Authority issued Nov. 29, 2012, in PCT/EP12/069937 filed Oct. 9, 2012.

*Primary Examiner* — Brenda Coleman
(74) *Attorney, Agent, or Firm* — Oblon, McClelland, Maier & Neustadt, L.L.P

(57) ABSTRACT

The present invention relates to a process for the preparation of 17-substituted steroids and, more particularly, to an improved method of synthesizing abiraterone or derivatives thereof in high yield and purity by means of a key 3-formate intermediate.

20 Claims, No Drawings

PROCESS FOR PREPARING 17-SUBSTITUTED STEROIDS

The present invention relates to a process for the preparation of 17-substituted steroids and, more particularly, to an improved method of synthesizing abiraterone or derivatives thereof in high yield and purity by means of a key 3β-formyloxy intermediate.

BACKGROUND OF THE INVENTION

Abiraterone acetate, chemically designated as (3β)-17-(3-pyridinyl)-androsta-5,16-dien-3-yl acetate of formula

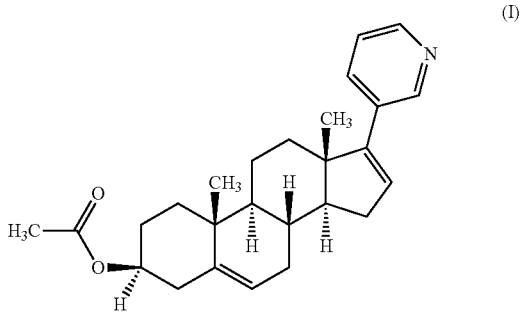

(I)

is a prodrug which is converted in vivo to abiraterone, 17-(3-pyridyl)-androsta-5,16-dien-3β-ol.

Abiraterone is a potent inhibitor of human cytochrome $P450_{17\alpha}$, a potential target enzyme in the treatment of hormone-dependent prostatic carcinoma.

Abiraterone acetate is the active ingredient of the approved drug (Zytiga®) which is administered in a solid oral dosage form (250 mg tablet).

Zytiga® in combination with prednisone is indicated for the treatment of patients with metastatic castration resistant prostate cancer (CRPC) who have received prior chemotherapy containing docetaxel.

Literature reports several processes for the preparation of abiraterone or derivatives thereof.

Synthetic approaches to abiraterone generally start from a dehydroepiandrosterone-3-acetate substrate.

Abiraterone was first described in patent application EP 0633893 (BTG International Ltd.) covering 16,17-ene-17-(3-pyridyl) steroids as a class of compounds useful in the treatment of androgen- and oestrogen-dependent disorders. EP' 893 reports two synthetic routes which comprise replacing a 17-oxo ketone residue in its enol form by a leaving group in a Palladium complex-catalysed cross-coupling reaction with a pyridyl ring-substituted boron compound. Said replacement can be via steroidal enol triflate or a halo derivative. Particularly, in the specific experimental work, abiraterone acetate is prepared from dehydroepiandrosterone-3-acetate substrate via triflating in the presence of 2,6-di-t-butyl-4-methylpyridine; the triflate intermediate is purified by column chromatography to separate the unreacted and the triene impurity and then isolated from hexane. The pyridine moiety was inserted in the steroid nuclea by a palladium catalysed cross-coupling of the enol triflate derivative by using diethyl-(3-pyridyl)-borane in aqueous THF with sodium carbonate as nucleophilic activator. Chromatography, again, is required to give the desired compound. However, it has been observed that the overall yield of the process is low (around 48%) and chromatography appears to be the only tool able to provide a substantially pure product which is then crystallised from apolar solvents and, optionally, used in the downstream of the process.

EP 0721461 (BTG International Ltd.) describes an improved method for the preparation of (3β)-acyloxy-16,17-ene-17-(3-pyridyl) steroids; especially, the preferred compound (3β)-acetoxy-17-(3-pyridyl)-androsta-5,16-diene is prepared via a vinyl iodide intermediate by using the unprotected (3β)-hydroxy compounds as substrate. The application reports that triflates are expensive starting materials and so an alternative route is desirable; in addition, the triflating reaction has to be carried out on the 3-acetate as protecting group, said 3-acetate being, then, hydrolysed to the 3-ol in a separate step. However, the estimated overall yield starting from dehydroepiandrosterone is low (around 41%) and, mainly, a final purification by reverse phase chromatography is required.

WO 2006/021776 (BTG International Ltd.) describes novel salt forms of $C_2$-$C_4$ acyl esters of abiraterone or a derivative thereof and to a process for the preparation of abiraterone or a salt or derivative thereof. The application provides for an alternative method whereby a salt of the desired compound is recovered from a suitable solvent; operatively, the product of the triflate reaction is used in the Suzuki coupling unpurified. Salt isolation is meant to eliminate undesired by-product (triene) as well as unreacted starting material which remain in solution so as to simplify the purification process; expensive and time-consuming chromatography steps are to be avoided. The preferred salt is abiraterone acetate methanesulfonate which is, preferably, recovered from methyl tert-butyl ether.

WO 2006/021777 (BTG International Ltd.) describes a process for the preparation of abiraterone or $C_2$-$C_4$ acyl esters of abiraterone or a derivative thereof which comprises a triflating step by which a ketone of formula (II) is converted into a triflate of formula (III):

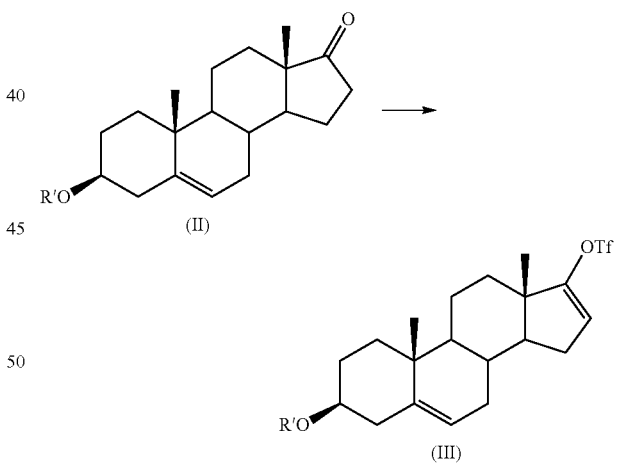

wherein R' is hydrogen or a lower acyl group having 2 to 4 carbon atoms; the triflating step being conducted in the presence of a base comprising a tertiary or heterocyclic amine such that the pKa of the conjugate acid at 25° C. is within the range 5.21 to 12. The application reports that known prior art recommend the use of 2,6-di-tert-butyl-4-methylpyridine in the triflating step since simple bases can lead to the formation of undesirable by-product. Particularly, the inventors observed that by using specific 2,6-di-tert-butyl-4-methylpyridine when triflating lower acyl protected substrate, elimination of the acid occurred giving an undesired triene by-product of formula (IV)

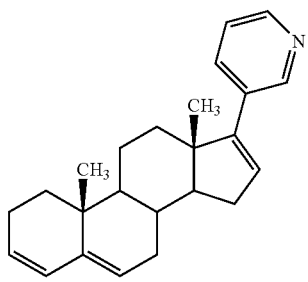

Subsequent coupling as well as isolation steps to abiraterone acetate are carried out by following the teachings of the International application WO '776 above. However, the estimated overall yield of the process starting from dehydroepiandrosterone 3-acetate is very low (around 32%) with a purity around 97%; isolation as, inter alia, mesylate salt entails an additional neutralization and optionally crystallization step(s) with further loss in yield.

Furthermore, Chinese application CN 101768199 discloses abiraterone acetate polymorphs A, B, C and D; methods of preparing said polymorphs comprise recrystallizing abiraterone acetate which is separated and purified by a chromatographic column in different solvents.

PURPOSE OF THE INVENTION

It results from the prior art that in order to prepare 16,17-ene-17-(3-pyridyl) steroid derivatives several methods have been proposed.

However, it appears that said methods are poor in yield, difficult to scale up and/or particularly expensive.

Generally, none of these methods appears to be suitable for a reliable and economic industrial application by suffering from significant cost and procedural drawbacks.

Particularly, processes to abiraterone commonly lead to specific by-products which are difficult to remove by conventional techniques as well as they make use of unattractive chromatographic systems in so far as poor yields and low purity profile are reported in the literature.

Hence, it would be desirable to study alternative efficient methods for preparing pure abiraterone with good yields and under conditions more favourable from the industrial application point of view.

It would further be desirable to obtain a highly pure active ingredient and to limit the formation of undesirable by-products.

SUMMARY OF THE INVENTION

We have now, surprisingly, found an easy and efficient synthesis of abiraterone via a key 3β-formyloxy intermediate which allows to overcome the drawbacks of the processes described in the prior art.

DETAILED DESCRIPTION OF THE INVENTION

Therefore, an object of the present invention is a process for preparing abiraterone which comprises:

a) triflating a compound of formula (V)

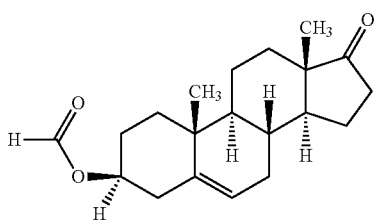

in the presence of a base to give a compound of formula (VI)

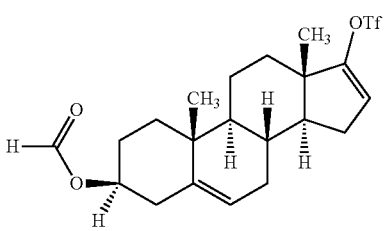

b) contacting crude compound of formula (VI) with a 3-pyridyl borane derivative under Suzuki cross-coupling conditions to give the abiraterone 3β-formyloxy ester of formula (VII)

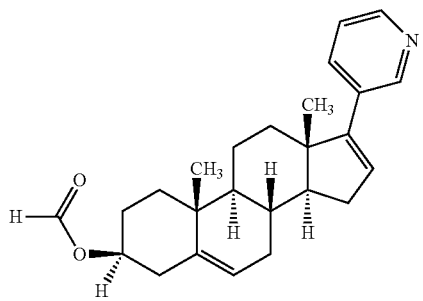

c) hydrolysing the crude abiraterone 3β-formyloxy ester of formula (VII); and
d) isolating the so obtained abiraterone from an alcoholic solvent.

Dehydroepiandrosterone (hereinafter DHEA) is a well known commercially available intermediate in the preparation of steroids or analogues thereof, whose preparation is extensively described in the art.

According to the invention DHEA is protected as DHEA 3-formyloxy ester of formula (V) by known techniques. For instance, DHEA 3-formyloxy ester is obtained in quantitative yield by reacting DHEA with formic acid at room temperature; work up procedure gives an organic layer which can be used in subsequent triflating Step a).

Step a:
The triflate compound of formula (VI) is prepared by reacting DHEA 3-formyloxy ester of formula (V) with an enol ester forming trifluoromethanesulphonic acid derivative in the presence of a base in accordance with known techniques.

Triflating reactions are well known to the skilled person, particularly, specific steroidal enol activation according to the invention is well described in the art.

Operatively, trifluoromethanesulfonic anhydride and a base are simultaneously added to a solution of DHEA 3-formyloxy ester of formula (V) in the presence of an organic solvent at room temperature (about 20-25° C.). After 1 hour at room temperature, the mixture is quenched preferably with saturated NaHCO₃.

The preferred enol ester forming trifluoromethanesulphonic acid derivative is trifluoroethanesulfonic anhydride.

Preferred bases according to the invention are triethylamine, 2,6-lutidine and methylimidazole.

Preferably, the triflating step is carried out in the presence of an organic solvent.

Preferred solvents are hydrocarbon solvents, more preferably chlorinated hydrocarbons, dichloromethane being preferred.

Such reaction occurs with 80-85% conversion rate, yielding a mixture of triflate derivative (molar yield: 70%-75%) and unreacted DHEA 3-formyloxy (15%-20% molar yield).

The main step impurity, triene derivative, is maintained at very low level (<3% by area % HPLC).

In a preferred embodiment of the invention, DHEA 3-formyloxy is used and added simultaneously with 1 equivalent of an organic base and 1.1 equivalent of triflic anhydride. Such conditions allow both an optimal conversion of the DHEA formate and a high purity of the crude triflate intermediate.

Moreover, it has been observed that diluting the mixture increases the molar yield of the triflate derivative; lowering temperature of reaction limits the formation of impurities but slow down the kinetic of the reaction and decreases the conversion rate.

The formation of impurities increases with the reaction time.

Step b:

The crude compound of formula (VI) is contacted with a 3-pyridyl borane derivative under Suzuki cross-coupling conditions to give the abiraterone 3 formyloxy ester of formula (VII).

Cross-coupling reactions are well known to the skilled person, particularly, the insertion of aromatic moieties on steroid nuclea by cross-coupling reaction is well described in the art.

For instance, EP 0633893 describes a palladium catalysed cross-coupling of pure enol triflate derivative of formula (VI) by using diethyl-(3-pyridyl)-borane in aqueous THF with sodium carbonate as nucleophilic activator.

Operatively, crude triflate compound of formula (VI) is reacted with a suitable (3-pyridyl)-borane derivative in the presence of a Palladium catalyst complex and a polar solvent under Suzuki condition.

The general procedure comprises refluxing a mixture of the pyridylborane derivative, triflate derivative, palladium catalyst and aqueous sodium carbonate over 1-4 h to give abiraterone 3 formyloxy ester of formula (VII).

The preferred (3-pyridyl)-borane derivative is diethyl-(3-pyridyl)-borane.

Preferred solvents are polar aprotic solvents, THF and methyl-THF being preferred.

The preferred catalyst is Bis(triphenylphosphine)palladium dichloride.

In a preferred embodiment of the invention, step b) Suzuki coupling is performed by contacting a crude compound of formula (VI) with diethylpyridylborane in the presence of a Pd catalyst, preferably PdCl₂(PPh₃)₂ and an aqueous sodium carbonate solution to give the crude abiraterone 3-formyloxy ester of formula (VII).

Preferably, 1.1 equivalents of 3-pyridylborane derivative, notably diethyl(3-pyridyl)borane, with respect to the estimated pure triflate derivative is used. The Pd catalyst is then removed by filtration from a hydrocarbon solution, a toluene solution being preferred.

It has been observed that high temperature of reaction (e.g. the reflux temperature of the mixture) favours conversion rate.

Step c:

Crude abiraterone 3β-formyloxy ester of formula (VII) is hydrolysed by known methods.

Operatively, the organic layer coming from step b) is concentrated under vacuum and crude abiraterone 3β-formyloxy is hydrolyzed, preferably under basic conditions.

In a preferred embodiment of the invention, crude abiraterone ester is hydrolyzed in a methanol/mineral base solution where sodium hydroxide or sodium carbonate are preferred.

Step d:

Pure abiraterone is isolated by direct crystallization from alcoholic solvent.

Operatively, crude abiraterone 3β-formyloxy is hydrolyzed in an alcoholic solution and abiraterone is isolated by filtration.

In a preferred embodiment of the invention, abiraterone is crystallized from methanol in overall yield of around 50% from the DHEA starting material.

Abiraterone is then optionally re-crystallized from a mixture of hydrocarbon and alcoholic solvent. Preferably, abiraterone is re-crystallized from a methanol/dichloromethane mixture.

The product is obtained in good yield and with very high purity.

As above described the process of the invention foresees conducting step b) and step c) on a crude substrate; operatively, organic layers coming from step a), triflating, as well as step b), coupling, are concentrated and crude residues so obtained are directly used in the subsequent reactions.

It has been observed that said crude residue comprises around 15-20% by weight of unreacted DHEA 3β-formyloxy and DHEA respectively.

Isolation step d) entails that unreacted DHEA remains in the mother liquor in as much as it can be recovered from the alcoholic, preferably methanolic, solution in accordance with known techniques.

Therefore, a further object of the invention is a process for preparing abiraterone as above further comprising recovering unreacted DHEA from the alcoholic solution as in isolation step d).

DHEA is, then, protected as DHEA 3β-formyloxy derivative, crystallized and reused in step a) (recovery yield: 6-10%).

Operatively, mother liquor from step d) which comprises the unreacted DHEA is concentrated to dryness; the residue is then allowed to react with formic acid to give pure DHEA 3β-formyloxy compound of formula (V) after crystallization from, preferably, hexane.

Moreover, abiraterone is optionally converted into its 3β-acetoxy ester in accordance with known techniques.

In one embodiment of the invention, abiraterone is acetylated by using acetic anhydride in the presence of a base, preferably triethylamine, and purified in hexane and ethanol to give pure abiraterone acetate of formula (I) with an overall yield up to 43-45% from the DHEA and a high purity (up to 99.0% by HPLC). In this embodiment, charcoal and a chelating resin are advantageously added to the hexane and ethanol solution of abiraterone acetate; the reaction mixture is then filtered and the pure active ingredient is crystallized. Suitable chelating resins that can be used in the invention are immobilized resins such as complex phenol-formaldehyde based resins; the Hokuetsu brand type MA-A resin (available from Ajinomoto) being preferred.

By considering the recovery of the unreacted DHEA formate the overall yield increases up to 47%.

Therefore, a further object of the invention is a process for preparing abiraterone as above further comprising converting abiraterone into abiraterone acetate of formula (I).

A further object of the invention is the following compounds
(3β)-17-(3-pyridinyl)-androsta-5,16-dien-3-yl formate; and
(3β)-formyloxy-androsta-5,16-dien-17-yl-trifluoromethane-sulfonate;
as key intermediates in the preparation of a highly pure abiraterone.

It is thus evident how the method object of the invention constitutes a process suited for industrial production, efficient and economic synthetic alternative for the preparation of abiraterone and derivatives thereof.

The characterising feature of the invention resides in that triflating is performed on a 3β-formyloxy derivative.

To the best of inventors' knowledge, the introduction of the triflate leaving group on a 3β-formyloxy protected steroid nucleus is neither known in the art nor suggested by any prior art reference.

The prior art prompts the skilled person against triflating in the preparation of steroids which have a 17-heterocyclic substituent; he is directed towards alternative route, for instance, via vinyl iodide intermediate as described in EP' 461 above.

In addition, the prior art reports that triflating a lower acyl protected substrate leads to elimination of the acid giving an undesired triene by-product which cannot be removed by common recrystallization methods, as underlined in WO'776 above.

On the contrary, the present invention provides for triflating a protected steroid moiety as 3β-formyloxy derivative resulting in an almost quantitative conversion (around 85%) of a compound of formula (V) into a triflate compound of formula (VI).

Furthermore, it is worth noting that the main impurity (triene) described in the above patent applications is easily maintained at very low levels by the improvements of the invention.

Hence, such conditions entail both an optimal conversion of the DHEA formate and a high purity of the crude triflate intermediate; in turn, such a low impurity profile allows isolating pure abiraterone by direct crystallization from alcoholic solvent, preferably methanol.

Basic patent EP 0633893 describes a generic triflation of an acetyloxy derivative where ester hydrolysis by aqueous sodium hydroxide in the presence of methanol is carried out; however, chromatographic purification appears to be mandatory in order to obtain a suitable purity of the end-product.

EP 1789432 discloses isolating by salification and recovering from a couple of suitable solvents, methanesulfonate salt and MTBE being preferred; neutralization and optional crystallization are needed.

Thus, the process of the invention does not need either salt isolation and any purification by column chromatography as described in the art.

Abiraterone acetate is obtained with both higher yield and purity with respect to the known procedures (overall yield up to 45% from the DHEA, HPLC purity up to 99.0%).

Recovering the unreacted DHEA out of the triflating/coupling step further improves the overall yield in abiraterone acetate up to 47%.

In substance, the process of the invention provides for:
a. high conversion into triflate compound of formula (VI);
b. very low elimination to undesired triene by-product;
c. no chromatographic purification;
d. recovering unreacted DHEA; and
e. direct crystallization of the end-product in high yield and purity.

A practical embodiment of the process object of the present invention comprises protecting commercially available DHEA as the 3β-formyloxy ester of formula (V); triflating said compound of formula (V) in the presence of a base to give a crude compound of formula (VI) which undergoes Suzuki cross-coupling with a 3-pyridyl borane derivative; crude abiraterone 3-formyloxy ester of formula (VII) so obtained is hydrolyzed into abiraterone which is eventually crystallized from alcoholic solvents; abiraterone is then optionally converted into its 3β-acetoxy ester in accordance with known techniques.

A preferred practical embodiment of the process object of the present invention comprises protecting commercially available DHEA as 3β-formyloxy ester of formula (V) by reaction with formic acid; simultaneously adding said compound of formula (V) and a suitable organic base to triflic anhydride to give a crude compound of formula (VI); Suzuki cross-coupling is then carried out with a 3-pyridyl borane derivative, preferably diethylpyridyl borane, in the presence of a Palladium catalyst, preferably $PdCl_2(PPh_3)_2$, and an aqueous sodium carbonate solution to give crude abiraterone 3β-formyloxy ester; said 3β-formyloxy ester is hydrolyzed in a methanol/mineral base, preferably sodium hydroxide, solution to give abiraterone which is eventually crystallized from methanol and optionally recrystallized; unreacted DHEA is recovered from the methanolic solution; and abiraterone is optionally converted into its 3β-acetoxy ester in accordance with known techniques. For better illustrating the invention the following examples are now given.

Example 1

Synthesis of dehydroisoandrosterone-3-formate (DHEA formate)

A solution of 100 g (0.346 mole) of dehydroepisoandrosterone (DHEA) in 500 ml of formic acid 80-99% was maintained 4 hours at 20-25° C. and the end of the reaction was monitored by HPLC (area % of DHEA). The solution was then concentrated at 50° C. under vacuum (40 mbar). 500 ml of $CH_2Cl_2$ were added to the concentrate and 400 ml of saturated $NaHCO_3$ were added to the solution. The mixture was stirred for 30 minutes at 20-25° C. The two layers were then separated. The organic layer was washed with 100 ml of water. The organic layer was dehydrated and used as it was on the triflating stage. The yield was assumed to be 100% from the DHEA Example 2

Synthesis of 3β-formyloxyandrosta-5,16-dien-17-yl-trifluoromethanesulphonate (triflate compound)

To a solution of 100 g of DHEA formate (0.316 mole) in 1 l of $CH_2Cl_2$ were added simultaneously a solution of 98 g (1.1 eq.) of trifluoromethanesulfonic anhydride in 500 ml of $CH_2Cl_2$ and a solution of 34 g (1 eq.) of 2,6-lutidine in 500 ml of $CH_2Cl_2$, over about 1 hour, at a temperature of 20±2° C. Lutidine was charged once about 15% of triflic anhydride solution had been added. The mixture was stirred for 1 hour at 20±2° C. The mixture was cooled to 10-15° C., and a solution of 53 g of NaHCO$_3$ (2 eq.) in 1 l of water was added to the mixture at 10-15° C. over 15-30 minutes. The mixture was stirred for at least 1 hour at 20-25° C. Layers were then separated and the organic layer was washed with 0.2 l of water. The organic layer was concentrated at 35° C. under vacuum (40 mbar) to give 142 g of crude triflate compound which contained 100 g (by HPLC assay) of pure triflate compound (0.22 mole) and around 15 g of unreacted DHEA formate (0.047 mole). Yield in pure product (by HPLC assay) was around 70% from the DHEA.

$^1$H-NMR (CDCl$_3$): 8.0 ppm (1H, s, 20 [—HCO—]); 5.6 ppm (1H, dd, 10 [—CH—]); 5.4 ppm (1H, dd, 15 [—CH—]); 4.7 ppm (1H, m, 1 [—O—CH(CH$_2$—)$_2$—]); 1.0 ppm (3H, s, 19 [—CH$_3$]); 1.1 ppm (3H, s, 18 [—CH$_3$]). $^{13}$C (CDCl$_3$): 112-124 ppm C quaternary, q, 22 [—CF$_3$].

Example 3

Synthesis of Abiraterone

To a solution of 100 g (0.22 mole) of estimated pure triflate compound (by HPLC assay) in 1 l of THF were added 36 g (1.1 eq.) of diethyl (3-pyridyl)borane, and then 3 g (2 molar %) of bis(triphenylphosphine)palladium (II) chloride. A solution of 94 g (4 eq.) of Na$_2$CO$_3$ in 0.4 l of purified water was added to the mixture which was heated to reflux (65-67° C.) under efficient stirring (biphasic mixture) for a period of 30 minutes to 1 hour (IPC HPLC). The mixture was cooled to 15-20° C., and 1 l of toluene and then 1 l of water were added to the mixture which was stirred for a period of 10-15 minutes. The mixture was filtered through a bed of Clarcel® to remove the Pd catalyst and the two layers were separated. The aqueous layer was washed with 0.2 l of toluene. Organic layers were then washed with 0.1 l of water. The organic layer was concentrated at 35-40° C. under vacuum (20 mbar) to give the crude abiraterone formate which was hydrolysed in 380 ml of methanol with 160 g of 10% aqueous NaOH. The suspension was heated to 70-75° C. for a period of 1 h and a half to 2 h (IPC end of reaction: HPLC). The mixture was cooled to 20° C., then to 0-5° C. and maintained for 30 minutes at 0-5° C. The suspension was filtered and the cake was washed twice with 60 ml of water then washed with 200 ml of acetone cooled to 0-5° C. The wet crude stage 3, abiraterone, was dried at 40-45° C. under vacuum for 5 hours.
Purification 400 ml of CH$_2$Cl$_2$ and 300 ml of methanol were added to 100 g of crude stage 3. The mixture was heated to 40-45° C. (reflux) to give a solution. The CH$_2$Cl$_2$ was then removed by distillation at atmospheric pressure. The mixture was cooled to 0-5° C. and then maintained for 1 hour at 0-5° C. The suspension was filtered and the cake was washed twice with 100 ml of methanol cooled to 0-5° C. The wet stage 3, abiraterone, was dried at 40-45° C. under vacuum for 5 hours to give 63 g of pure product. At this step, the overall yield from the DHEA was around 50%.

3β-formyloxy-17-(3-pyridyl)androsta-5,16-diene $^1$H-NMR (CDCl$_3$): 8.6 ppm (1H, s, 24 [—CH— (pyr)]); 8.4 ppm (1H, dd, 25 [—CH— (pyr)]); 8.0 ppm (1H, s, 20 [—HCO—]); 7.6 ppm (1H, dd, 27 [—CH— (pyr)]); 7.2 ppm (1H, t, 26 [—CH— (pyr)]); 6.0 ppm (1H, s, 10 [—CH—]); 5.4 ppm (1H, dd, 15 [—CH—]); 4.7 ppm (1H, m, 1 [—O—CH(CH$_2$—)$_2$—]); 1.1 ppm (3H, s, 19 [—CH$_3$]); 0.9 ppm (3H, s, 18 [—CH$_3$]).

Example 4

Synthesis of Abiraterone Acetate 1 l of THF was added to 100 g of abiraterone (0.286 mole). 44 g (1.5 eq.) of triethylamine, 1.75 g of 4-dimethylaminopyridine (2 molar %) and 35 g (1.2 eq.) of acetic anhydride were added to the slurry. The slurry was stirred for 24 hours at 20-25° C. (the mixture turned to solution at the end of the reaction which was monitored by HPLC). 0.7 l of toluene and 0.4 l of water were added to the mixture which was stirred for 1 h at 20-25° C. The mixture was clarified on a cake of Clarcel®. The two layers were separated and the organic layer was washed with 0.1 l of water. The organic layer was concentrated at 40° C. to dryness under vacuum. 100 ml of ethanol and 900 ml of n-hexane were then added and the mixture was heated to 55-60° C. to dissolve (the solution was still cloudy). 5 wt % of 2S activated charcoal and 5 wt % of Clarcel® were added to the mixture which was maintained 30 minutes at 55-60° C. The Clarcel® and the charcoal were then filtered at 55-60° C. and washed twice with 0.1 l of ethanol. The ethanol was then partially removed by distillation under vacuum at 40±5° C. The mixture was cooled to 20° C., then to 0-5° C. and maintained 1 hour at this temperature. The suspension was filtered and the cake was washed twice with 0.1 l of n-hexane at 0-5° C. The wet abiraterone acetate was dried at 50° C. under vacuum to give 90 g (0.23 mole) of the pure abiraterone acetate (up to 99.0% by HPLC) 90% yield from the abiraterone. The overall yield from DHEA was around 43-45%.
Recovery of the Unreacted DHEA The mother liquor (from the abiraterone step described above) containing the unreacted DHEA was concentrated to dryness. The residue was then allowed to react with formic acid as described in Example 1 to give after crystallization in hexane pure DHEA formate in a 10% yield from the DHEA formate used in the triflating step. The purity of this DHEA formate was high enough to be used in the triflating step. Including the recovery of the unreacted DHEA formate, the overall yield of abiraterone acetate from DHEA was around 45% by weight.

Example 5

Synthesis of dehydroisoandrosterone-3-formate (DHEA formate)

A solution of 100 g (0.346 mole) of dehydroepisoandrosterone (DHEA) in 500 ml of formic acid 80-99% was maintained 4 hours at 20-25° C. and the end of the reaction was monitored by HPLC (area % of DHEA). The solution was then concentrated at 50° C. under vacuum (40 mbar). 500 ml of CH$_2$Cl$_2$ were added to the concentrate and 400 ml of saturated NaHCO$_3$ were added to the solution. The mixture was stirred for 30 minutes at 20-25° C. The two layers were then separated. The organic layer was washed with 100 ml of water. The organic layer was dehydrated and used as it was on the triflating stage. The yield was assumed to be 100% from the DHEA.

Example 6

Synthesis of 3β-formyloxyandrosta-5,16-dien-17-yl-trifluoromethanesulphonate (triflate compound)

To a solution of 98 g (0.346 mole) of triflic anhydride in 1 l of CH$_2$Cl$_2$ was added a mixture of 100 g (0.316 mole) of DHEA formate and 34 g (0.316 mole) of 2,6-lutidine in 1 l of $CH_2Cl_2$, over about 1 hour, at a temperature of 20±2° C. The mixture was stirred for 1 hour at 20±2° C. The mixture was cooled to 10-15° C., and a solution of 53 g of $NaHCO_3$ (2 eq.) in 1 l of water was added to the mixture at 10-15° C. over 15-30 minutes. The mixture was stirred for at least 2 hours at 20-25° C. The layers were then separated and the organic layer was washed with 0.2 l of water. The organic layer was concentrated at 35° C. under vacuum (40 mbar) to give 142 g of crude triflate compound which contained by HPLC assay 107 g of pure triflate compound (0.239 mole), and around 15 g of unreacted DHEA formate (0.047 mole). The yield in pure product (by HPLC assay) was around 75%.

Example 7

Synthesis of Abiraterone

To a solution of 100 g (0.22 mole) of estimated pure triflate compound (by HPLC assay) in 1 l of THF were added 36 g (1.1 eq.) of diethyl (3-pyridyl)borane, and then 3 g (2 molar %) of bis(triphenylphosphine)palladium (II) chloride. A solution of 94 g (4 eq.) of $Na_2CO_3$ in 0.4 l of purified water was added to the mixture which was heated to reflux (65-67° C.) under efficient stirring (biphasic mixture) over a period of 30 minutes to 1 hour (IPC HPLC). The mixture was cooled to 15-20° C., and 1 l of toluene and then 1 l of water were added to the mixture which was stirred for a period of 10-15 minutes. The mixture was filtered through a bed of Clarcel® to remove the Pd catalyst and the two layers were separated. The aqueous layer was washed with 0.2 l of toluene. The organic layers were then washed with 0.1 l of water. The organic layer was concentrated at 35-40° C. under vacuum (20 mbar) to give the crude abiraterone formate which was hydrolysed in 380 ml of methanol with 160 g of 10% aqueous NaOH. The suspension was heated to 70-75° C. over a period of 1 h and a half to 2 h (IPC end of reaction: HPLC). The mixture was cooled to 20° C., then to 0-5° C. and maintained 30 minutes at 0-5° C. The suspension was filtered and the cake was washed twice with 60 ml of water then washed with 200 ml of acetone cooled to 0-5° C. The wet crude stage 3, abiraterone, was dried at 40-45° C. under vacuum over 5 hours.

Purification 400 ml of $CH_2Cl_2$ and 300 ml of methanol were added to 100 g of crude stage 3. The mixture was heated to 40-45° C. (reflux) to give a solution. The $CH_2Cl_2$ was then removed by distillation at atmospheric pressure. The mixture was cooled to 0-5° C. and then maintained for 1 hour at 0-5° C. The suspension was filtered and the cake was washed twice with 100 ml of methanol cooled to 0-5° C. The wet stage 3, abiraterone, was dried at 40-45° C. under vacuum for 5 hours to give 63 g of pure product. The yield from the estimated pure triflate compound was around 70%. At this step, the overall yield from the DHEA was around 50% by weight.

Example 8

Synthesis of Abiraterone Acetate 1 l of THF was added to 100 g (0.286 mole) of abiraterone. 44 g (1.5 eq.) of triethylamine, 1.75 g of 4-dimethylaminopyridine (2 molar %) and 35 g (1.2 eq.) of acetic anhydride were added to the slurry. The slurry was stirred for 24 hours at 20-25° C. (the mixture turned to solution at the end of the reaction which was monitored by HPLC). 0.7 l of toluene and 0.4 l of water were added to the mixture which was stirred for 1 h at 20-25° C. The mixture was clarified on Clarcel®. The two layers were separated and the organic layer was washed with 0.1 l of water. The organic layer was concentrated at 40° C. to dryness under vacuum. 100 ml of ethanol and 900 ml of n-hexane were then added and the mixture was heated to 55-60° C. to dissolve (the solution was still cloudy). 5 wt % of 2S activated charcoal and 5 wt % of Clarcel® were added to the mixture which was maintained 30 minutes at 55-60° C. The Clarcel® and the charcoal were then filtered at 55-60° C. and washed twice with 0.1 l of ethanol. The ethanol was then partially removed by distillation under vacuum at 40±5° C. The mixture was cooled to 20° C., then to 0-5° C. and maintained 1 hour at this temperature. The suspension was filtered and the cake was washed twice with 0.1 l of n-hexane at 0-5° C. The wet abiraterone acetate was dried at 50° C. under vacuum to give 90 g (0.229 mole) of the pure abiraterone acetate (up to 99.0% by HPLC). The yield from abiraterone was around 90%. The overall yield from DHEA was around 43% by weight.

Recovery of the Unreacted DHEA

The mother liquor (from the abiraterone step described above) containing the unreacted DHEA was concentrated to dryness. The residue was then allowed to react with formic acid as described in Example 4 to give after crystallization in hexane pure DHEA formate in a 10% yield from the DHEA formate used in the triflating step. The purity of this DHEA formate was high enough to be used in the triflating step. Including the recovery of the unreacted DHEA formate, the overall yield in abiraterone acetate from the DHEA was around 47% by weight.

Example 9

Synthesis of dehydroisoandrosterone-3-formate (DHEA formate)

A solution of 25 g (86.7 mmol) of dehydroisoandrosterone in 125 ml (5 l/kg) of formic acid 99% was maintained 4 hours at 20-25° C. The end of the reaction was monitored by HPLC (area % of DHEA). The solution was then concentrated at 50° C. under vacuum (40 mbar). 125 ml (5 l/kg) of $CH_2Cl_2$ were added to the concentrate and 100 ml (4 l/kg) of saturated $NaHCO_3$ were added to the solution. The mixture was stirred for 30 minutes at 20-25° C. The two layers were then separated. The organic layer was washed with 25 ml (1 l/kg) of water. The organic layer was concentrated to give 27.4 g (yield 100%) of DHEA formate.

Example 10

Synthesis of 3β-formyloxyandrosta-5,16-dien-17-yl-trifluoromethanesulphonate (triflate compound)

To a solution of 14.7 g (52.1 mmol, 1.1 eq.) of trifluoromethanesulfonic anhydride in 150 ml of $CH_2Cl_2$ was added a solution of 15 g (47.4 mmol) of DHEA formate and 5.1 g (47.4 mmol, 1 eq.) of 2,6-lutidine in 150 ml of $CH_2Cl_2$, over about 1 hour, at a temperature of 20±2° C. The mixture was stirred for 1 hour at 20±2° C. The mixture was cooled to 10-15° C., and a solution of 8 g (94.8 mmol, 2 eq) of $NaHCO_3$ in 150 ml of water was added to the mixture at 10-15° C. over 15-30 minutes. The mixture was stirred for at least 1 hour at 20-25° C. The layers were then separated and the organic layer was washed twice with a solution of 60 ml of water and 1.1 g (23.7 mmol) of formic acid 99% and then twice with 30 ml of water. The organic layer was concentrated to give 21.6 g (yield 100%) of crude triflate compound. The molar yield calculated with the HPLC assay of the crude product was 71.3% from the DHEA.

Example 11

Synthesis of Abiraterone

To a solution of 13.8 g (30.7 mmol) of triflate compound (19.7 g crude product) in 138 ml of THF were added 4.9 g (33.8 mmol, 1.1 eq.) of diethyl (3-pyridyl)borane, and then 0.43 g (0.6 mmol, 2 molar %) of bis(triphenylphosphine)palladium (II) chloride. A solution of 13 g (123 mmol, 4 eq.) of $Na_2CO_3$ in 55.2 ml of purified water was added to the mixture which was heated to reflux (65-67° C.) under efficient stirring (biphasic mixture) over a period of 30 minutes to 1 hour (the end of the reaction was monitored by HPLC area %). The mixture was cooled to 15-20° C., and 138 ml of toluene and 138 ml of water were added to the mixture which was stirred over a period of 10-15 minutes. THF was removed by concentration under vacuum. The mixture was filtered through a bed of Clarcel® and the two layers were separated. The aqueous layer was washed with 27.6 ml of toluene. The organic layers were then washed with 13.8 ml of water. The organic layer was concentrated at 40-45° C. under vacuum and 58 ml of methanol and 24.7 g (61.8 mmol, 2.01 eq) of 10 wt % NaOH were added to the crude product. The mixture was heated to 70° C. over a period of 30 minutes to 1 hour, then cooled to 5-10° C. and maintained 30 minutes to 1 hour at this temperature. The suspension was then filtered and the cake was washed first with methanol, then with water and finally with acetone. The wet solid was dried at 40-45° C. under vacuum for 5 hours to give 9.2 g (yield 85.5%) of crude stage 3 (abiraterone).
Purification 34.8 ml of $CH_2Cl_2$ and 26.1 ml of methanol were added to 8.7 g (24.9 mmol) of crude stage 3 (abiraterone). The mixture was heated to 40-45° C. (reflux), to have a solution. The $CH_2Cl_2$ was then removed by distillation at atmospheric pressure. The mixture was cooled to 0-5° C., and then maintained 1 hour at 0-5° C. The suspension was filtered (fast filtration) and the cake was washed twice with 4.4 ml of methanol cooled to 0-5° C. The wet solid was dried at 40-45° C. under vacuum for 5 hours to give 7.2 g (yield of purification 82.8%) of pure stage 3 (abiraterone). The overall yield from DHEA was around 50%.

Example 12

Synthesis of Abiraterone Acetate 70 ml of THF were added to 7 g (20 mmol) of stage 3.3 g (30 mmol) of triethylamine, 0.12 g (1 mmol) of 4-dimethylaminopyridine (5 molar %) and 2.45 g (24 mmol) of acetic anhydride were added to the slurry. The slurry was stirred for 24 hours at 20-25° C. (the mixture turned to solution at the end of the reaction+IPC HPLC). 49 ml of toluene and 28 ml of water were added to the mixture which was stirred for 1 h at 20-25° C. The mixture was clarified on a cake of Clarcel®. The two layers were separated and the organic layer was washed with 3.5 ml of water. The organic layer was concentrated at 40° C. under vacuum. 8 ml of ethanol and 70 ml of n-heptane were added to the concentrate. The mixture was heated to 55-60° C. to dissolve (the solution was still cloudy). 0.4 g of 2S activated charcoal and 0.4 g of Clarcel® were added to the mixture which was maintained 30 minutes at 55-60° C. before being filtered at 55-60° C. The cake of Clarcel® on the filter was washed twice with 7 ml of ethanol. The ethanol was then removed by distillation under vacuum at 40±5° C. and n-heptane entrainments. The mixture was cooled to 20° C., then to 0-5° C. and maintained 1 hour at this temperature. The suspension was filtered and the cake was washed twice with 8 ml of n-heptane at 0-5° C. The wet solid was dried at 50° C. under vacuum to give 6.7 g (yield 85.4%) of abiraterone acetate. The overall yield from the DHEA was around 43%.

Example 13

Synthesis of dehydroisoandrosterone-3-formate (DHEA formate)

A solution of 45 g (156 mmol) of dehydroisoandrosterone in 225 ml (51/kg) of formic acid 80% was maintained 7 hours at 20-25° C. The end of the reaction was monitored by HPLC (area % of DHEA). The mixture was extracted with 90 ml of dichloromethane. The aqueous layer was then washed twice with 45 ml of dichloromethane. The organic layer was washed with 180 ml of saturated sodium bicarbonate solution and then with 45 ml of water. The organic layer was concentrated to give 49 g (yield 99.2%) of DHEA formate.

Example 14

Synthesis of 3β-formyloxyandrosta-5,16-dien-17-yl-trifluoromethanesulphonate (triflate compound)

To a solution of 46.6 g (165 mmol, 1.1 eq.) of trifluoromethanesulfonic anhydride in 430 ml of $CH_2Cl_2$ was added a solution of 47.5 g (150 mmol) of DHEA formate and 16.1 g (150 mmol, 1 eq.) of 2,6-lutidine in 215 ml of $CH_2Cl_2$, over about 1 hour, at a temperature of 20±2° C. The mixture was stirred for 1 hour at 20±2° C. The mixture was cooled to 10-15° C., and a solution of 16.4 g (195 mmol, 1.3 eq) of $NaHCO_3$ in 237.5 ml of water was added to the mixture at 10-15° C. over 15-30 minutes. The mixture was stirred for at least 1 hour at 20-25° C. The layers were then separated and the organic layer was washed twice with a solution of 190 ml of water and 3.5 g (75 mmol) of formic acid 99% and then twice with 47.5 ml of water. The organic layer was concentrated under vacuum to give crude triflate compound. The molar yield calculated with the HPLC assay of the crude product was 65% from the DHEA.

Example 15

Synthesis of Abiraterone

To a solution of 41 g (91.4 mmol) of triflate compound 100% in 287 ml of THF were added 14.8 g (100.5 mmol, 1.1 eq.) of diethyl (3-pyridyl)borane, and then 1.3 g (1.83 mmol, 2 molar %) of bis(triphenylphosphine)palladium (II) chloride. A solution of 38.7 g (365.6 mmol, 4 eq.) of $Na_2CO_3$ in 164 ml of purified water was added to the mixture which was heated to reflux (65-67° C.) under efficient stirring (biphasic mixture) over a period of 30 minutes to 1 hour (the end of the reaction was monitored by HPLC area %). The mixture was cooled to 15-20° C., and 328 ml of toluene and 328 ml of water were added to the mixture which was stirred over a period of 10-15 minutes. THF was removed by concentration under vacuum. The mixture was filtered through a bed of Clarcel® and the two layers were separated. The aqueous layer was washed with 82 ml of toluene. The organic layers were then washed with 41 ml of water. The organic layer was concentrated at 40-45° C. under vacuum and 172.5 ml of methanol and a solution of 19.5 g (184 mmol, 2.01 eq) of $Na_2CO_3$ in 69 ml of water were added to the crude product. The mixture was heated to 70° C. over a period of 30 minutes to 1 hour, then cooled to 20° C. 207 ml of $CH_2Cl_2$ were then added to the mixture which was stirred for 5 to 10 minutes and clarified. The two layers were then separated. The aqueous layer was washed with 34.5 ml of $CH_2Cl_2$ and the combined organic layers were washed with 34.5 ml of water. 34.5 ml of methanol were added to the organic layer and $CH_2Cl_2$ was removed by distillation at atmospheric pressure. The mixture was cooled to 0-5° C., and then maintained for 1 hour at 0-5° C. The suspension was filtered (fast filtration) and the cake was washed twice with 20 ml of methanol cooled to 0-5° C. The wet solid was dried at 40-45° C. under vacuum to give 27 g (yield 85%) of pure stage 3 (abiraterone). The overall yield from the DHEA was around 54.7%.

Example 16

Synthesis of Abiraterone Acetate 280 of THF were added to 28 g (80.1 mmol) of stage 3. 12.2 g (120.1 mmol) of triethylamine, 0.49 g (4 mmol) of 4-dimethylaminopyridine (5 molar %) and 9.8 g (96.1 mmol) of acetic anhydride were added to the slurry. The slurry was stirred for 24 hours at 20-25° C. (the mixture turned to solution at the end of the reaction+IPC HPLC). 196 ml of toluene and 112 ml of water were added to the mixture which was stirred for 1 h at 20-25° C. The mixture was clarified on a cake of Clarcel®. The two layers were separated and the organic layer was washed with 14 ml of water. The organic layer was concentrated at 40° C. under vacuum. 28 ml of ethanol and 252 ml of n-heptane were added to the concentrate. The mixture was heated to 55-60° C. to dissolve (the solution was still cloudy). 1.4 g of 2S activated charcoal and 1.4 g of Clarcel® were added to the mixture which was maintained 30 minutes at 55-60° C. before being filtered at 55-60° C. The cake of Clarcel® on the filter was washed twice with 28 ml of ethanol. Ethanol was then removed by distillation under vacuum at 40±5° C. and n-heptane entrainments. The mixture was cooled to 20° C., then to 0-5° C. and maintained 1 hour at this temperature. The suspension was filtered and the cake was washed twice with 28 ml of n-heptane at 0-5° C. The wet solid was dried at 50° C. under vacuum to give 26.7 g (yield 85%) of abiraterone acetate. The overall yield from the DHEA was around 46.5% by weight.

Example 17

Comparative Test 1

An additional comparative test was performed to show the main improvements of the invention. In accordance with Examples 5 to 8 of the invention abiraterone was prepared starting from dehydroisoandrosterone-3-formate (DHEA formate) by monitoring triflating step conversion rate, yields and triene decomposition. The same reaction conditions (steps: a to d) were, then, applied to the corresponding dehydroisoandrosterone-3-acetate (DHEA acetate) derivative. The comparative results are reported in the following Tables:

TABLE 1

| FORMATE ROUTE | Yield % | Conversion % | Purity % |
| --- | --- | --- | --- |
| Step a | 71 | 80 | Triene: 2.8 |
| Step b/c/d | 67 | | Triene: 0.6 |
| Overall | 48 | | Abiraterone: 99.1 |

TABLE 2

| ACETATE ROUTE | Yield % | Conversion % | Purity % |
| --- | --- | --- | --- |
| Step a) | 64 | 80 | Triene: 4.2 |
| Step b)/c)/d) | 61 | | Triene: 0.8 |
| Overall | 39 | | Abiraterone: 98.9 |

It results readily from Table 1 that starting from the new intermediate DHEA formate of formula (V) and following the procedure described in the experimental work according to the invention, we obtained abiraterone in higher yield and purity compared with known prior art methods.

As mentioned above, it is worth noting that said results were obtained by direct crystallization of abiraterone; no chromatographic purification or additional salt isolation were required.

Moreover, the results in Table 1 vs. Table 2 show how the new 3-formyl derivative of formula (V), compared with the most common 3-acetyl one, under the same reaction conditions which have been improved according to the present invention, allows obtaining pure abiraterone with clearly higher partial as well as overall yields. Particularly, triflating step a) occurred in high conversion rate by keeping triene impurity at very low level. Said purity of crude triflate compound of formula (VI) is suitable for isolating highly pure abiraterone by direct crystallization from alcoholic solvent; again, no isolation of intermediate salts was required.

Example 18

Comparative Test 2

An additional test was arranged in order to investigate the role of 3-formyl protecting residue in the specific triflating step a). Following reaction conditions reported in the art, 1.1 eq. of triflic anhydride were added to a solution of DHEA formate of formula (V) and 1.4 eq. of 2,6-di-tert-butyl-methylpyridine in 20 l/kg of $CH_2Cl_2$ over 10 to 15 minutes. The mixture was then maintained for 3 hours at 20° C. before being quenched with saturated $NaHCO_3$ to give a crude compound of formula (VI). The same conditions were then applied to the corresponding dehydroisoandrosterone-3-acetate (DHEA acetate).

The comparative results are reported in the following Tables:

TABLE 3

| FORMATE ROUTE | Yield % | Conversion % | Purity % |
| --- | --- | --- | --- |
| Step a) | 62.5 | 72.4 | Total impurities: 10<br>Triene: 9.85 |

TABLE 4

| ACETATE ROUTE | Yield % | Conversion % | Purity % |
|---|---|---|---|
| Step a) | 64.3 | 89.2 | Total impurities: 24.9<br>Triene: 14.9 |

The results in Table 3 vs. Table 4 show how the new 3-formyl derivative of formula (V) allows drastically reducing the amount of impurities; especially, triflating step a) occurred in high yield and conversion rate by limiting undesired triene by-product. Step a) was deliberately carried out with a base which the prior art does not identify as the best choice in the specific steroid activation according to the invention; WO' 777 page 11 Table 2 reported that under the most common triflating conditions a high amount of impurities, especially 17% of triene by-product, are obtained. Hence, the above data confirm the role of formate protecting residue in providing an improved impurity profile.

The invention claimed is:

1. A process for preparing abiraterone, comprising:
   a) triflating a compound of formula (V):

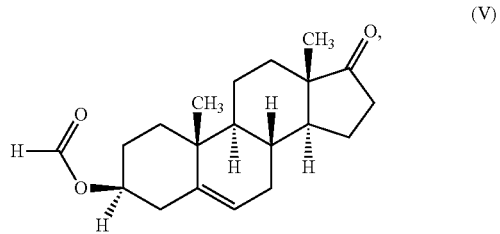

(V)

in the presence of a base to give a compound of formula (VI):

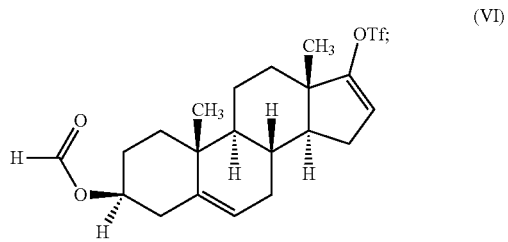

(VI)

b) contacting the crude compound of formula (VI) with a 3-pyridyl borane derivative under Suzuki cross-coupling conditions to give abiraterone 3β-formyloxy ester of formula (VII):

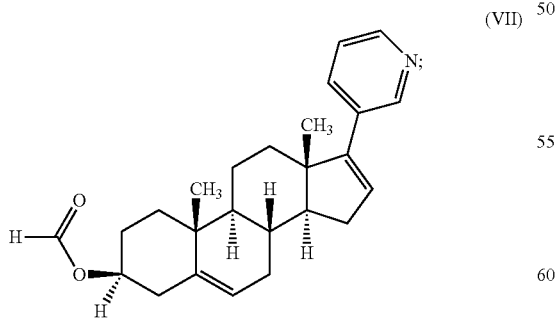

(VII)

c) hydrolysing the crude abiraterone 3β-formyloxy ester of formula (VII); and d) isolating a resulting abiraterone from an alcoholic solvent.

2. The process according to claim 1, wherein the base in the triflating a) is selected from the group consisting of triethylamine, methylimidazole and 2,6-lutidine.

3. The process according to claim 2, wherein the base is 2,6-lutidine.

4. The process of claim 1, wherein the triflating a) is carried out at room temperature.

5. The process of claim 1, wherein, in the triflating a), the compound of formula (V) is added simultaneously with 1 equivalent of an organic base and 1.1 equivalent of triflic anhydride.

6. The process of claim 1, wherein, in the contacting b), 1.1 equivalent of the 3-pyridyl borane derivative is contacted relative to 1 equivalent of the triflate compound of formula (VI).

7. The process of claim 1, wherein the contacting b) is carried out at the reflux temperature.

8. The process of claim 1, wherein the contacting b) is carried out in the presence of Bis(triphenylphosphine)palladium dichloride.

9. The process of claim 1, wherein the alcoholic solvent is methanol.

10. The process of claim 1, further comprising:
    converting the abiraterone into abiraterone acetate.

11. A process of claim 10, wherein the abiraterone acetate is crystallized from a hexane and ethanol solution.

12. A process of claim 11, wherein charcoal and a chelating resin are added to the hexane and ethanol solution of abiraterone acetate.

13. The process of claim 1, further comprising:
    recovering unreacted DHEA from the alcoholic solvent of the isolating d).

14. (3β)-17-(3-pyridinyl)-androsta-5,16-dien-3-yl formate.

15. (3β)-formyloxy-androsta-5,16-dien-17-yl-trifluoromethanesulfonate.

16. The process of claim 2, wherein the triflating a) is carried out at room temperature.

17. The process of claim 3, wherein the triflating a) is carried out at room temperature.

18. The process of claim 2, wherein, in the contacting b), 1.1 equivalent of the 3-pyridyl borane derivative is contacted relative to 1 equivalent of the triflate compound of formula (VI).

19. The process of claim 2, wherein the contacting b) is carried out at the reflux temperature.

20. The process of claim 2, wherein the contacting b) is carried out in the presence of Bis(triphenylphosphine)palladium dichloride.

* * * * *